United States Patent
Jalowayski

Patent Number: 5,743,256
Date of Patent: Apr. 28, 1998

[54] NOSTRIL CLOSURE MEANS

[76] Inventor: Alfredo A. Jalowayski, 6864 Lipman St., San Diego, Calif. 92122

[21] Appl. No.: 612,374

[22] Filed: Mar. 7, 1996

[51] Int. Cl.⁶ .................................................. A62B 18/02
[52] U.S. Cl. .......................... 128/201.18; 128/206.11; 128/207.18
[58] Field of Search ................. 128/201.18, 206.11, 128/207.18

[56] References Cited

U.S. PATENT DOCUMENTS

| | | | |
|---|---|---|---|
| 1,995,076 | 3/1935 | Perryman | 156/252 |
| 2,693,799 | 11/1954 | Herman, Jr. | 128/201.18 |
| 2,945,493 | 7/1960 | Herman, Jr. | 128/201.18 |
| 3,301,254 | 1/1967 | Schickedanz | 128/894 |
| 3,568,678 | 3/1971 | Pourguier et al. | 128/207.18 |
| 3,741,210 | 6/1973 | Johnston | 128/894 |
| 4,031,569 | 6/1977 | Jacob | 623/10 |
| 4,280,493 | 7/1981 | Council | 128/201.18 |
| 4,534,342 | 8/1985 | Paxa | 602/74 |
| 4,584,997 | 4/1986 | Delong | 128/207.18 |
| 4,823,789 | 4/1989 | Beisang | 128/207.18 |
| 4,887,597 | 12/1989 | Holland | 128/206.11 |
| 4,938,746 | 7/1990 | Etheredge, III et al. | 128/207.18 |
| 5,113,857 | 5/1992 | Dickerman et al. | 128/206.11 |
| 5,207,651 | 5/1993 | Snyder | 604/174 |
| 5,383,891 | 1/1995 | Walker | 606/196 |
| 5,391,179 | 2/1995 | Mezzoli | 606/196 |
| 5,419,762 | 5/1995 | Arick et al. | 604/26 |
| 5,555,890 | 9/1996 | Schaller | 128/206.11 |

*Primary Examiner*—Aaron J. Lewis
*Attorney, Agent, or Firm*—J. F. McLellan

[57] ABSTRACT

An adhesive nostril patch that is precision cut and punched to provide a central opening, and to provide edge margins configured to approximate the configuration of the margins of the nostril opening for adherence thereto in fluid tight relation, in combination with a length of tubing having one end diagonally cut to facilitate forcible insertion of the tubing into the central opening of the patch, and having the opposite end flanged to engage the adhesive side of the patch, whereby air from the nostril is constrained to flow into the tubing for measurement of its pressure by external pressure measurement equipment.

11 Claims, 1 Drawing Sheet

NOSTRIL CLOSURE MEANS

BACKGROUND OF THE INVENTION

1. Field of the Invention

The present invention relates to a nostril closure means comprising a nostril patch for use in applications such as rhinomanometry, collection of nasal lavage fluid, introduction of medicine into-the nasal cavity or nasopharynx area, and humidification, cleansing, and treatment of the nasal cavity.

2. Description of the Prior Art

Nasal airway obstruction is symptomatic of a number of nasal conditions whose diagnosis and evaluation are facilitated by rhinomanometry, which measures the degree of nasal airway resistance resulting from the obstruction.

Rhinomanometry requires simultaneous measurement of the airflow and the pressure gradient across the nasal cavity during a nasal breathing cycle. Two rhinomanometry methods are available for this purpose, active anterior rhinomanometry and posterior rhinomanometry, the anterior method being favored where circumstances permit because it is relatively simple to practice.

In practicing the anterior method, a close fitting mask having a pair of outlet ports is fitted over the nose and adjacent areas of the face. The mask has highly conformable or even air inflatable edge margins to establish a fluid tight fit. This is necessary to confine nasal exhalations to the mask interior, except for a limited or controlled flow of air through the outlet ports. These ports are connected to external measuring apparatus which calculates the amount and rate of nasal air flow and the pressure present during respiration.

Airflow through one of the nostrils is blocked by some form of closure means attached to the nostril. A length of tubing in communication with the nostril interior extends through the closure means and out of one of the mask ports for connection to exterior equipment designed to measure the pressure in that nostril.

The second nostril opening is unrestricted or left open so that air expelled from that nostril passes into the mask. The air in the mask is allowed to pass through a second length of tubing which extends out of the other mask port to external equipment designed to measure fluid flow, such as a pneumotachometer. This measurement establishes the amount and rate of fluid flow through the second nostril.

Once pressure and fluid flow are determined for one nostril, the procedure is repeated for the opposite nostril to measure the pressure and fluid flow for that nostril.

In practicing the active anterior rhinomanometry procedure just described, it is important that the nasal closure means and associated tubing be quickly and easily attachable to the nose in fluid tight relation without discomfort to the patient.

Various devices and methods exist in the prior art for doing this. One such method employs a resilient insert custom molded or shaped to conform to the interior of the nasal vestibule. The insert includes a central passage to receive pressure measurement tubing for applying air from the nostril interior to the exteriorly located equipment for measuring the nostril air pressure.

Unfortunately, shaping the insert to provide a reliable, pressure tight fit is tedious and time consuming. In an effort to reduce the amount of time required to accurately shape the insert, a variation of this method employed an insert made of compressible foam material. The foam material compressed slightly for a better fit, but it was still necessary to initially custom cut or shape the insert so that it generally approximated the shape and contour of the nostril interior and to retrim if the fit was not satisfactory.

A further variation on the foregoing method was to employ foam in strip form, rolling it onto the tubing until the diameter of the rolled foam was about that of the nasal vestibule. If the fit was not satisfactory, the excess foam had to be removed by snipping it away with a pair of scissors or the like. If too much were removed, a pressure leak would occur, and the whole process had to be repeated.

Another method used a nasal closure in the form of a flat section of adhesive tape or the like. The tape included an opening for the pressure measurement tubing, and it's margins were carefully trimmed and configured to insure an air tight attachment of the tape to the nose. This method had the same disadvantages as the previous methods in that the tape had to be carefully configured to prevent air leaks from occurring between the tape and the tube, and between the tape and the margins of the nostril opening. Any leakage ruined the accuracy of the pressure readings. In addition, the tape was sometimes ineffective to hold the tubing against axial slippage, either out of the nasal cavity, or inwardly into contact with the walls of the nasal cavity, with attendant discomfort to the patent.

As can be seen, the practice of any of these methods was usually quite time consuming and therefore not completely satisfactory to a busy medical technician or physician faced with the task of cutting and fitting a nasal closure several times in order to achieve the fit necessary to obtain accurate test results.

SUMMARY OF THE INVENTION

According to the present invention, a nostril closure means is provided which preferably comprises a precut, preconfigured adhesive nostril patch in combination with a precut length of tubing. Preferably a plurality of patches of different sizes and configurations are lightly adhered to a carrier strip from which a paramedic or physician can select a patch approximating the size and shape of the nostril of a particular patient.

Each patch is cut into the approximate configuration of a nostril opening, and each is made progressively larger to cover a range of nostril sizes. Each patch also includes an opening that is cut, punched or otherwise formed, preferably at the intersection of the long and short axes of the patch.

The opening is adapted to closely receive a length of tubing one end of which is cut on a bias to provide a punching or shearing end to make it easier to forcibly insert the tubing into the central opening. The tubing diameter is slightly larger than the central opening, which causes the margins of the central opening to closely grip the tubing. This tends to provide a fluid tight seal, and also constrain the tubing from slipping inwardly and causing discomfort to the patient, or slipping outwardly out of the nasal patch.

The other or inner end of the tubing is upset or otherwise formed to provide a margin or flange with a substantially flat underside. The underside engages the inner side of the patch and provides a fluid tight fit when the tube is forcibly inserted into position. The end flange also constrains the tubing from slipping outwardly and separating from the patch.

In summary, the foregoing arrangement makes it easy for a technician to select an appropriately shaped nostril patch, insert the proper length of tubing through the central opening in the patch, and lightly press upon the patch to adhere it to the margins of the nostril opening.

3

The combination of the present nostril patch and tubing is also useful in other procedures, such as the collection of nasal lavage fluid, the injection or introduction of medicine such as antibiotics into the nose, and the humidification and cleansing of the nose.

Other objects and features of the present invention will become apparent from the following more detailed description, taken in conjunction with the accompanying drawings.

DESCRIPTION OF THE PREFERRED EMBODIMENTS

Figure 1:
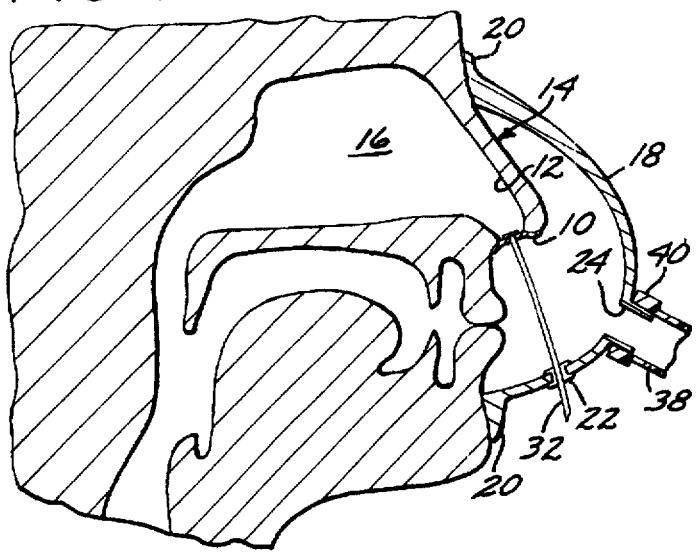
FIG. 1 is a cross-sectional view of a portion of the right side of a person's head, particularly including the nasal vestibule and the nostril opening, illustrating use of the present nostril patch in performing an active anterior rhinomanometry procedure.

Referring now to FIGS. 1–9, a nostril patch 10 is illustrated as it would appear when adhesively applied to the margins of a patient's nostril 12. As best seen in FIG. 1, the nostril 12 of the nose 14 opens into or includes a nasal vestibule or cavity 16 which is in communication with the sinuses and nasopharynx.

As previously mentioned, it is often important in the diagnosis and treatment of disorders of the nose to employ active anterior rhinomanometry for analysis of any nasal airway resistance. Comparison of airway resistance before and after corrective nasal surgery is especially useful in evaluating the success of such surgery. As will be seen, the present nose patch assembly facilitates the practice of rhinomanometry in such situations. Also, as will be described, it is also useful in collection of nasal lavage fluid, for introducing medicine into the nasal cavity of nasopharynx area, and for the humidification, cleansing and treatment of the nasal cavity.

Rhinomanometry involves blocking of the nostril 12 so that no airflow occurs through it, while leaving the other nostril (not shown) open so that normal respiration or a free flow of air can occur through it.

A face mask 18, tight fitting against the face at its edge margins 20, is fitted over the nose 14 and adjacent areas of the face, as best seen in FIG. 1. The edge margins could be air inflatable if desired to insure the desired pressure tight fit. The mask 18 includes a pair of outlet openings which define a pressure measurement port 22 and an airflow port 24. The port 24 is somewhat larger than the port 22, and is defined by a short, cylindrical section projecting from and integral with the wall defining the mask 18.

The nostril 12 is blocked by a closure preferably taking the form of the patch 10. The patch 10 is configured to approximate the shape of the margins of the nostril. Its configuration and dimensions vary according to the particular individual being tested or treated. Typically, the length of the nostril shaped patch would be approximately one and three eighths inches, and the width across the widest portion would be approximately three quarters of an inch.

Figure 9:
FIG. 9 is a top plan view, on a reduced scale, illustrating a carrier strip having a surface to which are separately adhered four of the patches of FIGS. 2–4.

Any suitable material may be used for the patch 10, such as materials commonly used for adhesive bandages or the like. Acceptable materials comprise a non-allergenic porous spunlaced polyester fabric layer 26 that is coated on one side with a porous acrylic adhesive 28 protected by a kraft release layer having a silicone release coating on one side. Such a combination of materials can be easily cut and punched to provide a patch 10 which will firmly adhere to the margins of the nostril 12 in fluid tight relation upon being lightly pressed in place. It is easily peeled away for removal, in the manner of a common adhesive bandage. Preferably four such patches of different sizes and configurations are separably adhered at their adhesive sides to a glossy surface of a carrier strip 29 for convenient marketing, as seen in FIG. 9.

Each patch 10 is also cut or punched to include a central opening 30 preferably located at the intersection of the short and long axes of the patch, where maximum airflow through the nostril is normally located. The diameter of the opening 30 is preferably made to conform to the circular shape of a length of pressure measurement tubing 32 and is smaller in diameter than the diameter of the tubing so that when the tubing is inserted into the opening the margins of the opening tightly press against the tubing in fluid tight relation. An opening diameter of 0.09 inch and a tubing outer diameter of 0.13 inch, with a tolerance of plus or minus ten percent, has been found to operate satisfactorily.

Figure 7:
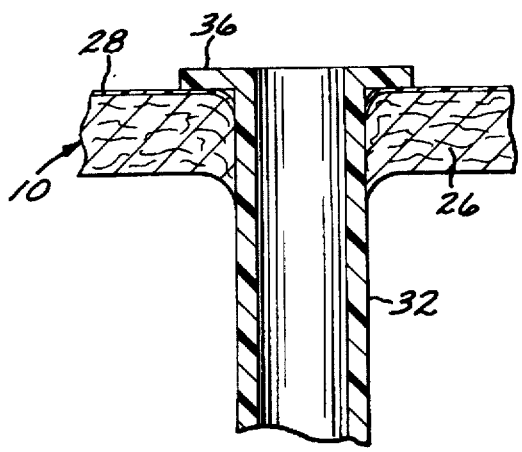
FIG. 7 is an enlarged cross-sectional view of the interengaged patch and tubing shown in FIG. 6.

The tubing 32 is made of non-allergenic polyester or similar plastic material that is provided at its outer end with an angled or bias cut 34 to facilitate forcible insertion of the tubing into the opening 30. The other or inner end of the tubing includes a flared end having a cap or flange 36, as best seen in FIG. 7.

A separate length of airflow measurement tubing 38, as seen in FIG. 1, is provided at its end with a collar or flange 40, or other suitable end termination, to provide a fluid tight fit between the tubing 38 and the outlet port 24 of the mask 18.

The flange 40 of the air flow measurement tubing 38 is adapted to tightly fit over a cylindrical outwardly projecting portion of the mask airflow port 24.

In operation, a suitably sized and configured patch 28 is selected. Next, the bias cut end of the pressure measurement tubing 32 is forcibly inserted through the opening 30 in the back or nonglossy side of the carrier strip 29, and through both layers 26 and 28 of the patch, respectively, while the patch is still adhered by adhseive 28 to the glossy surface of the carrier strip. The tubing is then pulled through the opening 30 until the underside of the flange 36 of the tubing touches the carrier strip. At this point, the patch 28 is peeled away from the backing sheet 29 and the flange 36 of the tubing is forced to break or tear through the carrier strip leaving the patch mounted to the flanged extremity of the tubing. The position of the patch is adjusted slightly by pushing it until its adhesive layer 28 is adhered to the underside of the flange 36 of the tubing, seen in FIGS. 6 and 7, thereby forming a fluid tight relation.

The patch 10, with the attached tubing 32, is then adhered to the margins of the nostril in fluid tight relation. In this position the flanged end of the tubing 32 will be in fluid communication with the nasal vestibule 16. The bias cut end of the tubing 32 is then pushed outwardly of the mask outlet port 22, leaving a generous length of tubing 32 remaining between the face and the mask. The mask is then moved toward the face and located over the nose in fluid tight relation with the face, while simultaneously pulling the excess tubing 32 outwardly from the mask.

The outer end of tubing 32 is next connected to a suitable pressure sensing device (not shown) for measuring the pressure in the nasal cavity 16. Similarly, a flow measuring device such as a pneumotachometer (not shown) is connected to the flow outlet port 24 for measuring the airflow from the mask, which is substantially equivalent to the airflow through the other nostril.

From the foregoing it will be seen that a properly sized and configured nose patch can be selected, and quickly and easily peeled off the carrier strip 29. The selected patch need not be tediously cut and trimmed at the time of performing a rhinomanometry procedure, and it can quickly and easily be attached by merely pressing it against the margins of the nostril. The prepunched tubing opening in the patch is already located in an optimum position, eliminating another time consuming operation normally performed just before the rhinomanometry procedure. The prepunched opening is also sized to closely accept the tubing in fluid tight relation when the bias-cut end of the tubing is inserted through the opening.

The flanged end of the tubing provides a fluid tight engagement with the patch, and serves as a stop to properly locate the tubing within the nasal vestibule.

All of the foregoing greatly simplifies the practice of rhinomanometry and the accuracy of the procedure.

Figure 8:
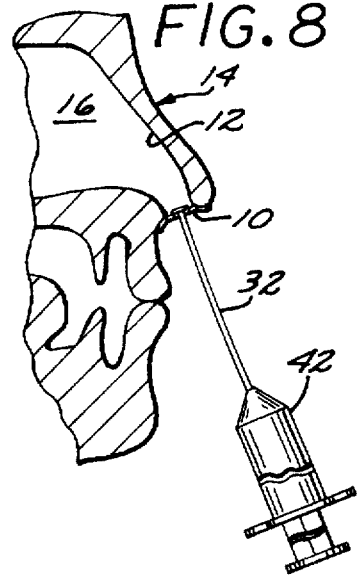
FIG. 8 is a view similar to FIG. 1, but illustrating the nostril patch being utilized in the collection of nasal lavage fluid.
Figure 2:
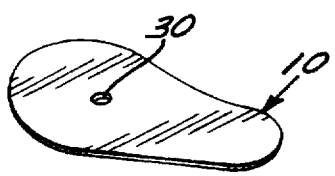
FIG. 2 is an enlarged perspective view of the nostril patch of the present invention.
Figure 5:
FIG. 5 is an enlarged perspective view of a length of pressure measurement tubing for use in conjunction with the nostril patch of FIG. 2, the length of tubing being illustrated as shorter than it actually is in order to fit within the drawing space.
Figure 6:
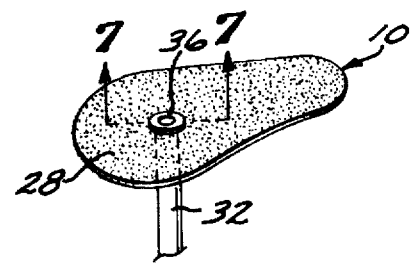
FIG. 6 is an enlarged perspective view of the nostril patch of FIG. 4 and showing a portion of the tubing of FIG. 5 extending outwardly from the patch.
Figure 3:
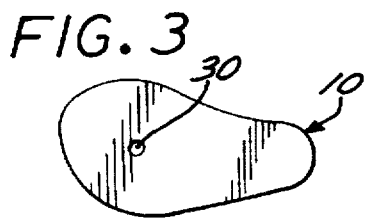
FIG. 3 is an enlarged plan view of the outer side of the patch of FIG. 2.
Figure 4:
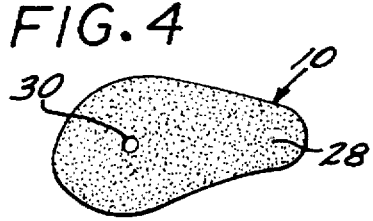
FIG. 4 is an enlarged plan view of the inner side of the patch of FIG. 2.

FIG. 8 illustrates use of the patch 10 in the collection of nasal lavage fluid.

In a typical prior art nasal lavage procedure about 10 ml of saline solution was instilled into each nostril, and then expelled into a funnel or reservoir for analysis of various chemical mediators indicative of some physiologic or pathologic process, such as allergic rhinitis. This prior art procedure was messy and undesirably released aerosol droplets with infectious organisms into the atmosphere. Further, because the patient had to hold his or her breath, with the head tiled backwardly, some of the solution was swallowed, and only about 50–60%. of the solution was recovered.

Utilizing the patch of the present invention, the tubing 22 is inserted into the patch 10 as before, and the patch 10 is adhered to the nostril margins to seal off the nostril. Saline solution can then be injected into the nostril quickly and smoothly by a syringe 42 inserted into the free end of the tubing 22. Using the same syringe, the saline solution is withdrawn from the nasal cavity by gentle suctioning, without dripping, messiness or loss of fluid.

In a typical instance, 5 cc of saline at 37 degrees C. contained in a 10 cc syringe was slowly injected into the nasal cavity with the patient's head tilted forward at about a 45 degree angle. The fluid was then withdrawn, and the process repeated as indicated. The procedure was repeated for the other nostril. Approximately 70–80% of the fluid was recovered, and the patient was able to breathe through the mouth during the procedure.

Another application for this same combination of elements is the instilling of medicine into the nose with the syringe 42. The medicine might be antibiotics instilled for the treatment of a recalcitrant infection in patients such as those with cystic fibrosis, or for the treatment of patients with atrophic rhinitis.

Yet another application for the patch 10, particularly for patients undergoing surgery such as septoplasty or endoscopic sinus surgery, is maintaining the nasal cavity of such a patient humidified for proper healing. Gentle humidification and removal of debris, and general cleansing are easily accomplished by using the described combination of patch 10, tubing 22 and syringe 42 containing a saline solution.

In summary, important and unique advantages result through use of the novel combination of a preconfigured and prepunched adhesive patch which is easily adherable to the margins of a nostril opening, and a length of tubing flared or flanged at one end and diagonally cut at the other end to facilitate its insertion into and through the patch.

While only a limited number of preferred embodiments of the invention have been described, persons skilled in the art to which it applies will readily perceive changes and modifications which may be made without departing from the spirit of the invention. Obviously, the invention may be used in other systems depending for utility upon quick and easy blockage of the nostril, except through a length of tubing. Other changes and modifications will be readily apparent to persons skilled in this art. Therefore, the invention is not intended to be limited except by the scope of the following appended claims.

What is claimed is:

1. Nostril closure means for controlling the flow of air through a nostril, the nostril closure means comprising:

a nostril patch having an adhesive side and preconfigured to approximate the configuration of the edge margins of a patient's nostril opening whereby adherence of the adhesive side of the patch to the edge margins of a patient's nostril opening blocks airflow past adhered portions of the nostril patch and the edge margins, the nostril patch including a prepunched tubing opening having a predetermined diameter; and a length of flexible tubing having a predetermined diameter and extending through the tubing opening to provide fluid communication with the interior of a patient's nose, the outside diameter of the tubing being greater than the diameter of the tubing opening in the nostril patch to thereby promote a fluid tight relation between the tubing and the portion of the nostril patch which defines the tubing opening, one end of the tubing being forcibly insertable through the tubing opening, the other end of the tubing having means for engaging the adhesive side of the nostril patch to provide a fluid tight relation.

2. Means according to claim 1 wherein the means for engaging the adhesive side of the patch comprises a flange.

3. Means according to claim 1 wherein the tubing is resilient whereby it is slightly compressible by the portion of the nostril patch which defines the tubing opening, thereby to promote a fluid tight relation between the tubing and the nostril patch.

4. Means according to claim 1 wherein the outer diameter of the tubing is approximately 0.13 inch and the diameter of the opening in the nostril patch is approximately 0.09 in.

5. Means according to claim 1 wherein the one end of the tubing is cut on a bias, and the other end of the tubing comprises a flange.

6. A nostril closure means for use in the practice of rhinomanometry, utilizing a mask adapted to fit over the nose in air tight relation with the face, the mask having a pair of outlet ports adapted for connection to external equipment for measuring airflow and pressure, the nostril closure means comprising:

a nostril patch having an adhesive side precut and configured for adhesion to and conformity with the edge margins of a patient's nostril opening, and further having a prepunched tubing opening of a predetermined diameter, and means for preventing airflow past adhered portions; and a length of flexible tubing disposed in fluid tight relation through the tubing opening, an outer diameter of the tubing being greater than the diameter of the tubing opening in the nostril patch whereby the tubing is compressed to facilitate establishment of the fluid tight relation.

7. A nostril patch according to claim 6 wherein the length of flexible tubing includes means at one end to constrain it from separation from the nostril patch.

8. A nostril patch according to claim 7 wherein the means comprises a flange.

9. A method for controlling the flow of air from a nostril opening such that only a portion of the air is communicated to pressure measurement equipment, the method comprising the steps of:

precutting and preconfiguring flat composite sheet material into a plurality of differently sized and configured nostril patches, each of which includes an adhesive layer and an edge margin configured to closely approximate the configuration of the edge portions of the nostril opening, and each patch having a tubing opening of a predetermined inside diameter;

providing a carrier strip to which the plurality of nostril patches are separably adhered;

selecting that one of the nostril patches which conforms most closely to the nostril opening and size of a particular individual, and peeling the selected nostril patch off the carrier strip;

cutting flexible tubing having an outside diameter larger than the inside diameter of the tubing opening in the selected nostril patch into a predetermined length of tubing;

inserting the inner end of the predetermined length of tubing into the tubing opening in communication with the interior of the nose, and in fluid tight relation with the portion of the nostril patch defining the tubing opening;

adhering the adhesive layer of the nostril patch edge margin to the edge portion of the nostril opening in fluid tight relation; and connecting the outer end of the length of tubing to pressure measuring equipment.

10. A method according to claim 9 and, after the inserting step, including the step of seating the inner end of the tubing in fluid tight relation upon the adhesive layer of the nostril patch.

11. In combination, a nostril patch having an adhesive side precut and configured for adhesion to and conformity with the edge margins of the nostril opening of an individual, and further having a prepunched tubing opening of a predetermined diameter through the nostril patch, the nostril patch including means for preventing airflow past adhered portions;

a length of flexible tubing having a predetermined diameter disposed through the tubing opening in fluid tight relation for communication with a patient's nasal cavity; the outer diameter of the tubing being greater than the diameter of the tubing opening in the nostril patch, a first end of the flexible tubing being attached to the nostril patch and a second end of the flexible tubing extending outwardly of the nostril patch; and a syringe coupled to the second end of the tubing for injecting fluid into a patient's nasal cavity.

* * * * *